United States Patent [19]

Konotsune et al.

[11] 4,036,631

[45] July 19, 1977

[54] PYRAZOLONE DERIVATIVES AND THEIR USE AS HERBICIDES

[75] Inventors: Takuo Konotsune; Katsuhiko Kawakubo, both of Tokyo, Japan

[73] Assignee: Sankyo Company Limited, Tokyo, Japan

[21] Appl. No.: 713,900

[22] Filed: Aug. 12, 1976

[30] Foreign Application Priority Data

Sept. 23, 1975  Japan .................................. 50-115344

[51] Int. Cl.² ...................... A01N 9/22; C07D 231/20
[52] U.S. Cl. ..................................... 71/92; 260/310 A
[58] Field of Search ......................... 260/310 A; 71/92

[56] References Cited

FOREIGN PATENT DOCUMENTS 2,513,750  10/1975  Germany

*Primary Examiner*—Donald B. Moyer
*Attorney, Agent, or Firm*—Toren, McGeady and Stanger

[57] ABSTRACT

Pyrazolone compounds of the formula

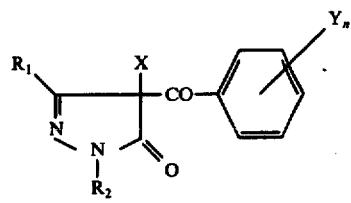

wherein $R_1$ represents a hydrogen atom or a lower alkyl group, $R_2$ represents a lower alkyl group or a lower alkenyl group, X represents a halogen atom, Y represents a halogen atom, a nitro group, a lower alkyl group or a lower alkoxy group, $n$ is an integer of 1 to 3 and when $n$ is 2 or 3, Y's may be the same or different. These compounds are useful as herbicides and obtainable by reacting the corresponding 5-pyrazolone derivatives with a halogenating agent.

25 Claims, No Drawings

PYRAZOLONE DERIVATIVES AND THEIR USE AS HERBICIDES

This invention relates to a new group of halogenopyrazolone derivatives and their use as herbicides.

More particularly, it is concerned with a pyrazolone derivative having the formula

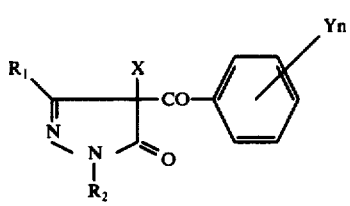

wherein $R_1$ represents a hydrogen atom or a lower alkyl group, $R_2$ represents a lower alkyl group or a lower alkenyl group, X represents a halogen atom, Y represents a halogen atom, a nitro group, a lower alkyl group or a lower alkoxy group, n is an integer of 1 to 3 and when n is 2 or 3, Y's may be the same or different, a herbicidal composition which comprises as an active ingredient the compound (I) and an agriculturally acceptable carrier, and a method for the destruction of undesirable weeds which comprises applying to said weeds a herbicidal amount of the compound (I). It is also concerned with a process for preparing the compound (I).

In the above general formula (I), $R_1$ represents preferably a straight or branched lower alkyl group having 1 to 6 carbon atoms, particularly 1 to 3 carbon atoms, such as methyl, ethyl, n-propyl, isopropyl, n-butyl, isobutyl, sec-butyl, tert-butyl, n-pentyl, isopentyl, sec-amyl, 2-methylbutyl, tert-amyl, n-hexyl, 2-hexyl, 2-methylpentyl, 3-methylpentyl, 4-methylpentyl, 3-hexyl, 2-ethylbutyl, 2-methyl-2-pentyl or 2,2-dimethylbutyl. $R_2$ preferably represents a straight or branched lower alkyl group having 1 to 6 carbon atoms, particularly 1 to 3 carbon atoms, as illustratively exemplified above in regard to the $R_1$ or a straight or branched lower alkenyl group having 3 to 6 carbon atoms, particularly 3 or 4 carbon atoms, such as 2-propenyl, 2-butenyl, 1-methyl-2-propenyl, 2-methyl-2-propenyl, 1-methyl-2-butenyl, 2-methyl-2-butenyl, 3-butenyl, 1-methyl-3-butenyl, 2-methyl-3-butenyl, 3-methyl-2-butenyl, 3-pentenyl, 2-hexenyl, 3-hexenyl or 4-hexenyl. X preferably represents a halogen atom, chlorine, bromine, fluorine or iodine. Y preferably represents a halogen atom as illustrated in regard to the X; a straight or branched lower alkyl group having 1 to 4 carbon atoms such as methyl, ethyl, n-propyl, isopropyl, n-butyl, isobutyl or tert-butyl or a straight or branched lower alkoxy group having 1 to 4 carbon atoms such as methoxy, ethoxy, n-propoxy, isopropoxy, n-butoxy or isobutoxy or a nitro group.

In the agricultural chemicals field, there were previously proposed various types of compounds as a herbicides and many of them have been nowadays practically utilized as an active ingredient in herbicidal compositions. However, there is a continuous demand for much more effective herbicidal compounds in the art.

As a results of our earnest studies on pyrazole ring-containing substances and their herbicidal activities, we have found that the pyrazole derivatives having the above formula (I) show prominent herbicidal activities.

With respect to the prior art found during the above-mentioned our studying, it is pointed out that only 4-benzoyl-1,3-dimethyl-5-hydroxy pyrazole and its utility as a chelating agent are disclosed in Chemische Berichte, 106, 332 – 338 (1973) and also that the synthesis of 1,3-dimethyl-4-(2-chlorobenzoyl)-5-hydroxypyrazole and 1,3-dimethyl-4-(4-nitrobenzoyl)-5-hydroxypyrazole is briefly disclosed without any indication of their properties, use, method of use, etc. in "The Chemistry of Heterocyclic Compounds" (Russian origin, 1972, No. 6, 799–804).

It is, accordingly, a primary object of this invention to provide a new group of pyrazolone derivatives (I) which show prominent herbicidal activities.

Another object of this invention is to provide an effective herbicidal composition containing compound (I).

In one aspect of this invention, there is provided a new group of pyrazolone derivatives having the formula (I) which are useful as herbicides.

In the compounds of the above formula (I), those wherein $R_1$ represents a methyl group, $R_2$ represents a methyl group or a 2-propenyl group, X represents a chlorine atom or a bromine atom, particularly a chlorine atom, Y represents a halogen atom, particularly a chlorine atom or a bromine atom, a methyl group, a nitro group or a methoxy group, n is 1 or 2 and, when n is 2, Y's may be the same or different, show a superior herbicidal activity. In particular, the compounds of the above formula (I) wherein $R_1$ represents a methyl group, $R_2$ represents a methyl group or a 2-propenyl group, X represents a chlorine atom or a bromine atom and Yn represents 2,4-dichloro or 2-chloro-4-nitro, are preferable.

Representative examples of the present compounds (I) are illustrated below, but they are not intended to limit the scope of this invention. The numbers of the compounds in the following list will be used hereinafter to identify the same compounds.

| Compound No. | Compound |
| --- | --- |
| 1. | 1,3-dimethyl-4-chloro-4-benzoyl-5-pyrazolone |
| 2. | 1,3-dimethyl-4-chloro-4-(2-chlorobenzoyl)-5-pyrazolone |
| 3. | 1,3-dimethyl-4-chloro-4-(2,4-dichlorobenzoyl)-5-pyrazolone |
| 4. | 1,3-dimethyl-4-bromo-4-(2,4-dichlorobenzoyl)-5-pyrazolone |
| 5. | 1,3-dimethyl-4-chloro-4-(3,4-dichlorobenzoyl)-5-pyrazolone |
| 6. | 1,3-dimethyl-4-chloro-4-(4-methylbenzoyl)-5-pyrazolone |
| 7. | 1,3-dimethyl-4-chloro-4-(2-methoxybenzoyl)-5-pyrazolone |
| 8. | 1,3-dimethyl-4-chloro-4-(4-nitrobenzoyl)-5-pyrazolone |
| 9. | 1,3-dimethyl-4-chloro-4-(4-bromobenzoyl)-5-pyrazolone |
| 10. | 1,3-dimethyl-4-chloro-4-(2-chloro-4-nitrobenzoyl)-5-pyrazolone |
| 11. | 1,3-dimethyl-4-chloro-4-(3,4-dimethoxybenzoyl)-5-pyrazolone |
| 12. | 1,3-dimethyl-4-chloro-4-(2-fluorobenzoyl)-5-pyrazolone |
| 13. | 1,3-dimethyl-4-chloro-4-(2,5-dichlorobenzoyl)-5-pyrazolone |
| 14. | 1,3-dimethyl-4-chloro-4-(4-tert-butylbenzoyl)-5-pyrazolone |
| 15. | 1,3-dimethyl-4-chloro-4-(3,4-dimethylbenzoyl)-5-pyrazolone |
| 16. | 1-methyl-4-chloro-4-(2-chlorobenzoyl)-5-pyrazolone |
| 17. | 1-methyl-3-ethyl-4-chloro-4-(2,4-dichlorobenzoyl)-5-pyrazolone |

| Compound No. | Compound |
|---|---|
| 18. | 1,3-dimethyl-4-chloro-4-(2-nitro-5-methylbenzoyl)-5-pyrazolone |
| 19. | 1-isopropyl-3-methyl-4-chloro-4-(2-chlorobenzoyl)-5-pyrazolone |
| 20. | 1,3-dimethyl-4-chloro-4-(2-iodobenzoyl)-5-pyrazolone |
| 21. | 1-ethyl-3-methyl-4-chloro-4-(2,4-dichlorobenzoyl)-5-pyrazolone |
| 22. | 1-(2-propenyl)-3-methyl-4-chloro-4-(2,4-dichlorobenzoyl)-5-pyrazolone |
| 23. | 1,3-dimethyl-4-chloro-4-(2,4-dichloro-5-methylbenzoyl)-5-pyrazolone |
| 24. | 1,3-dimethyl-4-bromo-4-(4-nitrobenzoyl)-5-pyrazolone |
| 25. | 1,3-dimethyl-4-chloro-4-(4-chlorobenzoyl)-5-pyrazolone |
| 26. | 1,3-dimethyl-4-chloro-4-(2-bromobenzoyl)-5-pyrazolone |
| 27. | 1,3-dimethyl-4-bromo-4-(2,4,5-trichlorobenzoyl)-5-pyrazolone |
| 28. | 1,3-dimethyl-4-chloro-4-(2-nitrobenzoyl)-5-pyrazolone |
| 29. | 1,3-dimethyl-4-chloro-4-(4-methoxybenzoyl)-5-pyrazolone |
| 30. | 1,3-dimethyl-4-bromo-4-(2-nitro-4-chlorobenzoyl)-5-pyrazolone |
| 31. | 1,3-dimethyl-4-bromo-4-(2-chlorobenzoyl)-5-pyrazolone |
| 32. | 1,3-dimethyl-4-bromo-4-(2-chloro-4-nitrobenzoyl)-5-pyrazolone |
| 33. | 1,3-dimethyl-4-chloro-4-(3-methylbenzoyl)-5-pyrazolone |
| 34. | 1,3-dimethyl-4-bromo-4-(3,5-dimethylbenzoyl)-5-pyrazolone |
| 35. | 1,3-dimethyl-4-bromo-4-(3-methyl-4-nitrobenzoyl)-5-pyrazolone |
| 36. | 1-(2-propenyl)-3-methyl-4-bromo-4-(2-chlorobenzoyl)-5-pyrazolone |
| 37. | 1-ethyl-3-methyl-4-bromo-4-(2-chloro-4-nitrobenzoyl)-5-pyrazolone |
| 38. | 1-methyl-4-bromo-4-(4-nitrobenzoyl)-5-pyrazolone |
| 39. | 1,3-dimethyl-4-iodo-4-(2,4-dichlorobenzoyl)-5-pyrazolone |

Among the above-listed pyrazolone compounds, there may be mentioned as a preferable group for herbicides in a paddy field those compounds having the Compound Nos. 3, 4, 18, 21 and 22 with those having the Compound Nos. 3, 4 and 18 being most preferable. Also, there may be mentioned as a preferable group for herbicides in an upland field those compounds having the Compound Nos. 3, 4, 10, 18, 21 and 22 with those having the Compound Nos. 3, 4 and 10 being most preferable.

The present compounds (I) are new substances not disclosed in literatures and can be easily prepared, for instance, by reacting a 5-pyrazolone derivative (II) with a halogenating agent as shown in the following chemical equation.

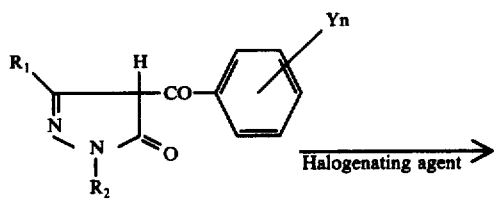

(II)

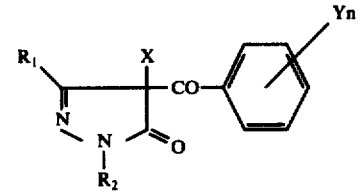

(I)

In the above formulae, $R_1$, $R_2$, X, Y and n are as defined above.

The above-mentioned reaction may be preferably effected in the presence of a solvent. Any solvents may be employed without particular restriction if they do not participate in the present reaction; for example, an ether or a mixture thereof, e.g., diethyl ether, tetrahydrofuran, diethylether-dioxane, tetrahydrofuran-dioxane and the like, an aromatic hydrocarbon, e.g., benzene, toluenes, xylenes and the like, a halogenated hydrocarbon, e.g., dichloromethane, chloroform, carbon tetrachloride and the like are mentioned and, especially, the aromatic hydrocarbon and carbon tetrachloride are preferably employed. Halogenating agents may include sulfuryl chloride, N-chlorosuccinimide, N-bromosuccinimide bromine, 1,5-dichloro-3,3-dimethylhydantoin, phosphorus pentachloride, iodine-potassium iodide and so on. Reaction temperature is not particularly critical and may be room temperature to a reflux temperature of the solvent employed. Reaction period of time may vary depending upon the reaction temperature and a sort of the reagent employed, but it is usually about 1 to 10 hours.

After completion of the reaction, the desired compound may be recovered from the reaction mixture in a conventional manner.

The starting compound (II) may be prepared, as shown below, according to the method which is disclosed in Japanese Patent Application No. 34939/1974 and No. 29939/1975.

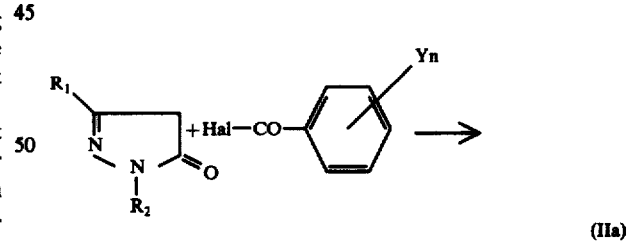

(IIa)

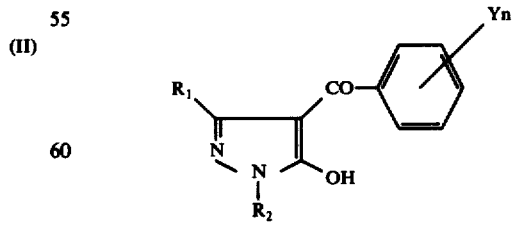

(II)

-continued

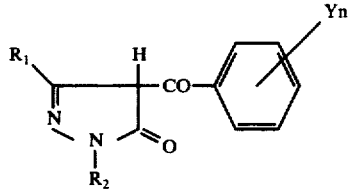

In the above formulae, $R_1$, $R_2$, Y and $n$ are as defined above.

The compounds of the above-mentioned formula (I) are utilized as herbicides and have a property of killing weeds by causing chlorosis.

In a paddy field, particularly prominent herbicidal effects against perennial weeds such as those of the family Cyperaceae, for example, "Hotarui" (*Scirpus hotarui* Ohwi.), "Mizugayatsuri" (*Cyperus serotinus* Rottb.) and the like and those of the family Alismataceae, for example, "Omodaka" (*Sagittaria trifolia* L.), "Urikawa" (*Sagittaria pygmaea* Miq.), which are difficult to control by the usual herbicides, can be achieved by pre- and post-emergence treatment in soil without any harmful effect on transplanted rice plants and growing rice plants. Also treatable are monocotyledonous weeds, such as, those of the family Gramineae, for example, barnyardgrass, panic grass and the like and broad-leaf weeds, such as, those of the family Scrophulariaceae, for example, false pimpernel, "Murasakisagigoke" (*Mazus miquelii* Makino), "Abunome" (*Dopatrium junceum* Hamilt.) and the like, those of the family Cruciferae, for example, wavy bittercress, marsh yellow cress, "Mizutagarashi" (*Cardamine lyrate Bunge*) and the like, those of the family Lythraceae, for example, toothcup, "Mizumatsuba" (*Rotala mexicana* Cham.) and the like and those of the family Compositae, for example, ragwort, American false daisy and the like.

In an upland field, pre- and post-emergence treatment in soils shows a particularly prominent effect against weeds of the family Caryophyllaceae, for example, common chickweed, Bog stichwort, mouse-ear chickweed, pearlwort and the like and, in addition, broad-leaf weeds, such as, those of the family Portulacaceae, for example, common purslane and the like, those of the family Amaranthaceae, for example, pigweed, rough pigweed and the like, those of the family Chenopodiaceae, for example, "Akaza" (*Chenopodium album* L.), common lamb's-quarters, "Koakaza" (*C. ficifolium* Smith) and the like, those of the family Commelinaceae, for example, asatic dayflower and the like, those of the famuly Labiatae, for example, henbit, "Kiranso" (*Ajuga decumbens* Thunb.) and the like, those of the family Oxalidaceae, for example, creeping wood sorrel, violet wood sorrel and the like, those of the family Leguminosae, for example, "Nekohagi" (*Lespedeza pilosa* Sieb et Zucc.), hairy vetch, common vetch and the like, those of the family Euphorbiaceae, for example, Virginia coperleaf, milk purslane and the like can be effectively controlled. And, narrow-leaf weeds, in particular, those of the family Cyperaceae, such as "Kayatsurigusa" (*Cyperus microiria* Steud.) and the like are effectively controlled and those of the family Gramineae such as wheatgrass, crab-grass, "Komehishiba" (*Digitaria timorensis* Balansa), barnyardgrass, green foxtail, "Akinoenokorogusa" (*Setaria Faberi* Herrmann), foxtail and the like are also effectively controlled.

On the other hand, crops such as rice plants, corns, sugar beets, soybeans, cotton plants, radishes, tomatoes, carrots, Chinese cabbages, lettuces and the like do not suffer from phytotoxicity.

Additionally, the compounds having the above-mentioned formula (I) are effectively usable as herbicides in an orchard, a non-crop land, a forest and so on.

The compounds in this invention may be formulated for use to the preparations commonly employed as a herbicide, for example, powdery dusts, coarse dusts, fine granules, granules, wettabble powders, emulsifiable concentrates, aqueous liquids, water soluble powders, oil suspensions and so on, with admixture of a carrier and, if required, other auxiliary agents. The carrier as used herein means a synthetic or natural and inorganic or organic substance that is mixed with on active compound and can assist an active compound in its arrival to the portion to be treated and make it easy to store, transport or handle.

As suitable solid carriers may be mentioned inorganic substances, such as, clays, which may be represented by Kaolinite, Montmorillonite or Attapulgite, talc, mica, pyrophyllite, pumice, vermiculite, gypsum, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum, and the like, waxes, such as, carnauba wax, beeswax and the like or urea.

As suitable liquid media or carriers may be mentioned paraffin or naphthene hydrocarbons, such as, kerosine, mineral oil, spindle oil, white oil and the like, aromatic hydrocarbons, such as, benzene, toluene, xylene, ethylbenzene, cumene, methylnapthalene and the like, chlorinated hydrocarbons, such as, carbon tetrachloride, chloroform, trichloroethylene, monochlorobenzene, o-chlorotoluene and the like, ethers, such as, dioxane, tetrahydrofuran and the like, ketones, such as, acetone, methylethylketone, diisobutylketone, cyclohexanone, acetophenone, isophorone and the like, esters, such as, ethyl acetate, amyl acetate, ethylene glycol acetate, diethylene glycol acetate, dibutyl maleate, diethyl succinate and the like, alcohols, such as, methanol, n-hexanol, ethylene glycol, diethylene glycol, cyclohexanol, benzyl alcohol and the like, ether alcohols, such as, ethylene glycol ethyl ether, ethylene glycol phenyl ether, diethylene glycol ethyl ether, diethylene glycol butyl ether and the like polar solvents, such as, dimethylformamide, dimethylsulfoxide and the like or water.

As the surface active agents used for emulsifying, dispersing, wetting, spreading, binding, controlling disintegration, stabilizing active ingredient, improving fluidity, rust proofing and so on may be utilized any of non-ionic, anionic, cationic and amphoteric ones, but non-ionic and/or anionic agents are usually employed. Suitable non-ionic suface active agents which may be mentioned are, for example, polymerization adducts of ethylene oxide to higher alcohols, such as, lauryl alcohol, stearyl alcohol, oleyl alcohol and the like, polymerization adducts of ethylene oxide to alkyl phenols, such as, isooctyl phenol, nonyl phenol and the like, polymerization adducts of ethylene oxide to alkyl naphthols, such as, butyl naphthol, octyl naphthol and the like, polymerization adducts of ethylene oxide to higher fatty acids, such as, palmitic acid, stearic acid, oleic acid the the like, polymerization adducts of ethylene oxide to mono- or di-alkyl phosphoric acids such as stearyl phosphoric acid, dilauryl phosphoric acid and the like, polymerization adducts of ethylene oxide to amines, such as dodecyl amine, stearic acid amide and the like, polymerization adducts of ethylene oxide to higher fatty acid esters of polyhydric alcohols, such as, sorbitan and said fatty acid esters, polymerization adducts of ethylene oxide to propylene oxide and so on. Suitable anionic surface active agents which may be mentioned are, for example, alkyl sulfate salts, such as, sodium lauryl sulfate, oleyl sulfate amine salt and the like, alkyl sulfonate salts, such as, sodium dioctyl sulfosuccinate, sodium 2-ethylhexene sulfonate and the like, aryl sulfonate salts, such as, sodium isopropylnaphthalene sulfonate, sodium methylenebisnaphthalene, sulfonate, sodium ligninsulfonate, sodium dodecylbenzene sulfonate and the like.

Moreover, the herbicidal compositions of this invention may be used in combination with high molecular compounds or other auxiliary agents, such as, casein, gelatin, albumin, glue, sodium alginate, carboxymethyl cellulose, methyl cellulose, hydroxyethyl cellulose, polyvinyl alcohol and the like for improving properties and increasing biological effects thereof.

The above-mentioned carriers and various auxiliary agents may be optionally utilized alone or in combination therewith for desired purposes, with consideration for the type of a preparation, application and other factors.

Dusts usually contain, for example, 1 to 25 parts by weight of the active compound and the remainder is a solid carrier.

Wettable powders usually contain, for example, 25 – 90 parts by weight of the active compound and the remainder is a solid carrier and a dispersing and wetting agent, if required, together with a protective colloidal agent, a thixotropic agent, an anti-foaming agent and the like.

Granules usually contain 1 – 35 parts by weight of the active compound and a major portion of the remainder is a solid carrier. The active compound is homogeneously admixed with the solid carrier or adhered or adsorbed on the carrier surface and the size of a granule is about 0.2 – 1.5 mm.

Emulsifiable concentrates usually contain, for example, 5 – 50 parts by weight of the active compound and about 5 – 20 parts by weight of an emulsifying agent, the remainder being a liquid carrier, if required, together with a corrosive inhibitor.

The herbicidal compositions of this invention, which are formulated into various types of preparations as above, may be applied in a paddy or upland field at 10 – 2000 g, preferably 100 – 500 g of the active ingredient per 10 a. for pre- or post-emergency soil treatment to control weeds effectively. Also, weeds can be unselectively controlled in non-crop land, such as, road, ground, house site, railroad and the like, at an application rate of the active ingredient of 200 – 4000 g per 10 a.

The herbicidal compositions of this invention may be preferably combined with other herbicides for broader herbicidal spectra and, in some cases, a synergistic effect is expectable. As examples of such other herbicides may be mentioned, for instance, triazine type herbicides such as 2-methylthio-4,6-bisethylamino-1,3,5triazine; 2-chloro-4,6-bisethylamino-1,3,5-triazine; 2-methoxy-4-ethylamino-6-isopropylamino-1,3,5-triazine; 2-chloro-4-ethylamino-6-isopropylamino-1,3,5-triazine; 2-methylthio-4,6-bis(isopropylamino)-1,3,5-triazine; 2-methylthio-4-ethylamino-6-isopropylamino-1,3,5-triazine and the like, phenoxy type herbicides, such as, 2,4-dichlorophenoxyacetic acid and its methyl, ethyl or butyl ester; 2-chloro-4-methylphenoxyacetic acid; 4-chloro-2-methylphenoxyacetic acid, ethyl 2-methyl-4-chlorophenoxybutyrate and the like, diphenyl ether type herbicides, such as, 2,4,6-trichlorophenyl-4'-nitrophenyl ether; 2,4-dichlorophenyl-4'-nitrophenyl ether; 3,5-dimethylphenyl-4'-nitrophenyl ether; 2,4-dichlorophenyl-3'-methoxy-4'-nitrophenyl ether and the like, urea type herbicides such as 3-(3,4-dichlorophenyl)-1-methoxy-1-methylurea; 3-(3,4-dichlorophenyl)-1,1-dimethylurea; 3-(4-chlorophenyl)-1,1-dimethylurea and the like, carbamate type herbicides, such as, 3-methoxycarbonylaminophenyl-N-(3-methylphenyl)-carbamate; isopropyl N-(3-chlorophenyl)carbamate; methyl N-(3,4-dichlorophenyl)carbamate and the like, uracil type herbicides, such as, 5-bromo-3-sec-butyl-6-methyluracil; 1-cyclohexyl-3,5-propyleneuracil and the like, thiolcarbamate type herbicides, such as, S-(4-chlorobenzyl)-N,N-diethylthiolcarbamate; S-ethyl N-cyclohexyl-N-ethylthiol carbamate; S-ethyl-hexahydro-1H-azepine-1-carbothioate; S-ethyl-N,N-di-n-propylthiocarbamate and the like, pyridinium salt type herbicides, such as, 1,1'-dimethyl-4,4'-bispyridinium dichloride and the like, phosphorus type herbicides, such as, N-(phosphonomethyl)glycine and the like, aniline type herbicides, such as, $\ominus,\ominus,\ominus$-trifluoro-2,6-dinitro-N,N-dipropyl-p-toluidine; 4-(methylsulfonyl)-2,6-dinitro-N,N-dipropylaniline, $N^3,N^3$-diethyl-2,4-dinitro-6-trifluoromethyl-1,3-phenyldiamine and the like, acid anilide type herbicides, such as, 2-chloro-2',6'-diethyl-N-(butoxymethyl) acetanilide; 2-chloro-2',6'-diethyl-N-(methoxymethyl)acetanilide; 3,4-dichloropropionanilide and the like, 5-tert-butyl-3-(2,4-dichloro-5-isopropoxyphenyl)-1,3,4-oxadiazolin-2-one; 2-(N-isopropyl-N-(4-chlorophenyl)carbamoyl)-4-chloro-5-methyl-4-isoxazolin-3-one; 3-isopropylbenzo-2-thia-1,3-diazinon-(4)-2,2-dioxide; 3-(2-methylphenoxy)-pyridazine and the like, but they are not critical.

The herbicidal compositions of this invention may be also applied with an admixture of plant growth regulators, such as, sodium naphthyl acetate; N-methoxycarbonyl-N'-4-methylphenylcarbamoylethylisourea; 1-(4-chlorophenylcarbamoyl)-3-ethoxycarbonyl-2-methylisourea; 1,2-dihydropyridazine-3,6-dione; gibberellins and the like; phthalimide type fungicides, such as, N-(2,6-diethylphenyl)-phthalimide; N-(2,6-diethylphenyl)-4-methylphthalimide and the like, pyridazinone type fungicides, such as, 6-(3,5-dichloro-4-methylphenyl)-3(2H)pyridazinone; 6-(3,4-dichlorophenyl)-3(2H)pyridazinone; 6-(3,5-dibromo-4-methylphenyl)-3(2H)pyridazinone; 6-(3-chloro-4-methyl-5-bromophenyl)-3(2H)pyridazinone; 6-(3,5-dichloro-4-methoxyphenyl)-3(2H)pyridazinone; 6-(3,5-dichloro-4-methylphenyl)-4,5-dihydro-3(2H)pyridazinone; 6-(3,4-dichlorophenyl)-4,5-dihydro-3(2H)pyridazinone; 6-(3,5-dibromo-4-methylphenyl)-4,5-dihydro-3(2H)pyridazinone; 6-(3-chloro-4-methyl-5-bromophenyl)-4,5-dihydro-3(2H)pyridazinone; 6-(3,5-dichlorophenyl)-4,5-dihydro-3(2H)pyridazinone and the like, other fungicides, such as, methyl 1-(butylcarbamoyl)-2-benzimidazolecarbamate; 1,2-bis(3-methoxycarbonyl-2-thioureido)benzene; 3-hydroxy-5-methylisoxazole; N-2,3-dichlorophenyltetrachlorophthamidic acid; 5-methyl s-triazole(3,4b)benzthiazole;

0,0-diisopropyl-S-benzylphosphorothioate; pentachloronitrobenzene; Kasugamycin; Blasticidin S; 4,5,6,7-tetrachlorophthalide and the like, insecticides, such as, 0,0-diethyl 0-(2-isopropyl-4-methyl-6-pyrimidinyl)phosphorothioate; 0,0-diethyl S-2((ethylthio)ethyl)phosphorodithioate; 1-naphthyl N-methylcarbamate; 0,0-dimethyl 0-(3-methyl-4-nitrophenyl)thiophosphate; 0,0-dimethyl S-(N-methylcarbamoylmethyl)phosphorodithioate; S-methyl-N-((methylcarbamoyl)oxy)thioacetoimidate; 0,0-dimethyl S-(N-methyl-N-formylcarbamoylmethyl)phosphorodithioate; 0,0-dimethyl S-2-(ethylthio)ethylphosphorodithioate; 0,0-diethyl S-2((ethylthio)ethyl)phosphorodithioate; 0,0-dimethyl-1-hydroxy-2,2,2-trichloroethylphosphonate, milbemycin and the like or fertilizers so on.

Preparation of the compounds have the above general formula (I) are illustrated hereinbelow by the following Examples.

EXAMPLE 1

1,3-Dimethyl-4-chloro-4-benzoyl-5-pyrazolone

To a solution of 2.16 g of 1,3-dimethyl-4-benzoyl-5-pyrazolone in 20 ml of dry benzene was added 1.62 g of sulfuryl chloride and the mixture was stirred at room temperature for 4 hours. After completion of the reaction, water was added to the reaction mixture and after shaking an organic layer was separated. The organic layer was washed successively with a saturated aqueous solution of sodium hydrogencarbonate and water, dried over anhydrous sodium sulfate and the solvent was distilled off from the solution. The so obtained residue was recrystallized from n-hexane to give 0.2 g of the desired product melting at 70.5° – 72° C. (Yield 7.6%)

Analysis for (%) $C_{12}H_{11}ClN_2O_2$ Calculated: C, 57.49; H, 4.43; N, 11.18; Cl, 14.14; Found: C, 56.97; H, 4.49; N, 10.46; Cl, 13.63.

EXAMPLE 2

1,3-Dimethyl-4-chloro-4-(2-nitro-5-methylbenzoyl)-5-pyrazolone

To a suspension of 2.65 g of 1,3-dimethyl-4-(2-nitro-5-methylbenzoyl)-5-pyrazolone in 20 ml of dry benzene was added 1.62 g of sulfuryl chloride and the mixture was stirred at room temperature for 4 hours. After completion of the reaction, the reaction mixture was treated in the same manner as in the Example 1 to give 2.0 g of the desired product melting at 110° – 111° C. (Yield 64.72%)

Analysis for (%) $C_{13}H_{12}ClN_3O_4$ Calculated: C, 50.41; H, 3.90; N, 13.57; Cl, 11.45; Found: C, 50.58; H, 3.89; N, 13.80; Cl, 11.38.

EXAMPLE 3

1,3-Dimethyl-4-bromo-4-(2,4-dichlorobenzoyl)-5-pyrazolone

To a solution of 0.285 g of 1,3-dimethyl-4-(2,4-dichlorobenzoyl)-5-pyrazole in 5 ml of carbon tetrachloride was added 0.356 g of N-bromosuccinimide and the mixture was heated under reflux for 1.5 hours. After cooling, the reaction mixture was filtered and the solvent was distilled off from the filtrate under reduced pressure. The so obtained residue was recrystallized from n-hexane to give 0.32 g of the desired product melting at 89° – 90° C. (Yield 85.9%).

Analysis for (%) $C_{12}H_9BrCl_2N_2O_2$ Calculated: C, 39.59; H, 2.49; N, 7.70; Br. 21.95; Cl, 19.48; Found: C, 40.08; H, 2.59; N, 7.83; Br, 21.72; Cl, 19.29.

Following any of the procedures in the above Examples 1 – 3, there were produces the following compounds.

1,3-dimethyl-4-chloro-4(2,4-dichlorobenzoyl)-5-pyrazolone, mp 83° – 84° C 1,3-dimethyl-4-chloro-4-(2-chloro-4-nitrobenzoyl)-5-pyrazolone, mp 74° – 75° C 1,3-dimethyl-4-chloro-4-(3,4-dimethoxybenzoyl)-5-pyrazolone, mp 107° – 108° C 1-ethyl-3-methyl-4-chloro-4-(2,4-dichlorobenzoyl)-5-pyrazolone, mp 54° – 55° C 1-(2-propenyl)-3-methyl-4-chloro-4-(2,4-dichlorobenzoyl)-5-pyrazolone, mp 54° – 55° C 1,3-dimethyl-4-bromo-4-(4-nitrobenzoyl)-5-pyrazolone, mp 125° – 126° C Examples of the preparations of the present herbicidal composition are given below. All parts are given by weight hereinafter unless otherwise stated.

EXAMPLE 4

Granules

70 Parts of the compound designated as Compound No. 3 are finely pulverized and 30 parts of clay are added thereto. The mixture is blended in a mixer to form a premix. 10 Parts of the premix are homogeneously blended with 60 parts of clay and 30 parts of bentonite in a mixer. To the resulting blend is added an appropriate amount of water. The mixer is kneaded in a kneader, extruded through a screen having a diameter of 0.8 mm. and dried in a draft drier at 50° C. The so obtained product is adjusted by a shifter to give granules.

EXAMPLE 5

Granules 35 parts of the compound designated as Compound No. 4 and 35 parts of S-(4-chlorobenzyl)N,N-diethylthiolcarbamate are finely pulverized and 30 parts of white carbon are added thereto. The mixture is blended in a mixer to form a premix. 20 parts of the premix are homogeneously blended with 50 parts of clay and 30 parts of bentonite in a mixer. To the resulting blend is added an appropriate amount of water. The mixture is kneaded in a kneader, extruded through a screen having a diameter of 0.8 mm. and dried in a draft drier at 50° C. The so obtained product is adjusted by a shifter to give granules.

Example 6

Wettable powders 50 parts of the compound designated as Compound No. 18, 29 parts of clay, 10 parts of diatomaceous earth, 5 parts of white carbon, 3 parts of sodium ligninsulfonate, 2 parts of "Newcoal" 1106 (trade name of a surfactant available from Nihon Nyukazai K.K., Japan) and 1 part of polyvinyl alcohol are homogeneously blended in a mixer and pulverized three times by means of a hammer mill to give wettable powders.

EXAMPLE 7

Emulsifiable concentrates 20 parts of the compound designated as Compound No. 21, 65 parts of xylene and 15 parts of "Paracoal" PS (trade name of a surfactant available from Nihon Nyukazai K.K., Japan) are blended and homogeneously dissolved to form emulsifiable concentrates.

In order to demonstrate an excellent herbicidal effect of the present herbicidal compositions thus prepared, experiments are given below. The wettable powders prepared according to the procedures in the above-mentioned Example 6 are used in the following experiments, each containing 50% by weight of the active compound of this invention,

EXPERIMENT 1

Water surface application tests for paddy field weed control 3 polyethylene pots (hereinafter abbreviated as A, B and C), each having the surface of 45 cm², were packed with paddy field soil. In Pot A were transplanted rice seedlings (two plants) (variety: Kinmaze at 2.5 leaf stage) and two tubers of "Urikawa" as a representative of perennial weed. In Pot B, seeds of monochoria, false pimpernel and "Abunome" (*Dopatrium junceum* Hamilt) as representatives of broad-leaf weed were incorporated in the soil, a block of runners of slender spikerush was transplanted thereinto and two tubers of "Mizagayatsuri" as a perennial weed were planted in the soil. In Pot C, seeds of barnyardgrass and "Hotarui" (*Scirpus hotarui* Ohwi) as representatives of narrow-lead weeds were incorporated in the soil and two tubers of "Omodaka" as a perennial weed were planted in the soil. The Pots A, B and C were kept in a green house for 3 days under paddy field conditions. After rooting of the plants, suspensions of test chemicals were applied into the paddy water at 10 ml. per pot. After 20 days from the treatment, herbicidal effects on each weed and phytotoxicity to rice plant were observed and evaluated. The results are shown in Table 1 wherein effective dose (g/a) means the minimum dose for growth inhibition rate to each test plant (percentage of leaf area suffering chlorosis) of not less than 70%.

EXPERIMENT 2

Pre-emergency application tests for upland weed control

In a polyethylene pot having the surface of 150 cm² were filled soil and seeds of cockspur-grass, crabgrass, green foxtail, goose grass and barnyardgrass as representatives of narrow-leaf weed were sown and covered with soil.

Another polyethylene pot having the surface of 150 cm² was filled with soil and seeds of asatic dayflower as narrow-leaf weed and common chickweed, pigweed, common pursland and common lambsquarters as representatives of broad-leaf weed were sown and covered with soil.

Immediately after soil-covering, suspensions of test compounds were applied to soil surface at the rate of 10 ml. per pot. After 20 days from the application, herbicidal effects on each weed were observed. The results are shown in Table 2 wherein ratings for evaluation are the same as in Experiment 1 and shown by means of effective dose (g/a).

Table 2

| | Herbicidal activity in field by pre-emergency application | | | | | | | | | |
|---|---|---|---|---|---|---|---|---|---|---|
| Compound No. | barnyard grass | crab-grass | goose grass | green foxtail | cockspur-grass | common chickweed | asatic dayflower | pigweed | common pursland | common lambsquarters |
| 3 | 75 | 200 | 75 | 50 | 100 | 25 | 50 | 75 | 25 | 25 |
| 4 | 75 | 100 | 100 | 100 | 100 | 25 | 200 | 25 | 25 | 25 |
| 10 | 75 | 100 | 50 | 50 | 50 | 25 | 100 | 100 | 75 | 50 |
| 11 | 100 | 200 | 200 | 75 | 100 | 50 | 100 | 100 | 50 | 25 |
| 18 | 75 | 200 | 75 | 100 | 50 | 25 | 25 | 100 | 25 | 25 |
| 21 | 75 | 200 | 100 | 50 | 75 | 25 | 50 | 50 | 25 | 25 |
| 22 | 100 | 75 | 75 | 100 | 50 | 25 | 50 | 25 | 50 | 25 |

It will be apparent from the above results that the pyrazole compounds (I) in this invention have excellent herbicidal activities and thus they are practically useful as herbicide for paddy field, upland field, non-crop land and so on.

What is claimed is:

1. A compound having the formula

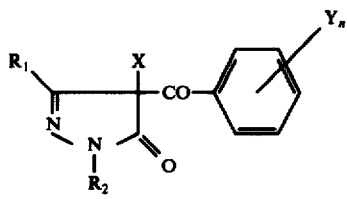

wherein $R_1$ represents a hydrogen atom or a lower alkyl group, $R_2$ represents a lower alkyl group or a lower alkenyl group, X represents a halogen atom, Y repre- Table 1

| | Herbicidal Activity in Paddy Field (Effective dose g/a) | | | | | | | |
|---|---|---|---|---|---|---|---|---|
| Compound No. | Barnyard-grass | Broad-weed leaf | "Hotarui" | "Urikawa" | Slender spikerush | "Mizugaya-tsuri" | "Omodaka" | Rice seedling transplanted |
| 7 | 50 | 75 | 100 | 50 | 100 | 75 | 100 | >800 |
| 3 | 12.5 | 12.5 | 6.25 | 6.25 | 6.25 | 6.25 | 6.25 | 400 |
| 4 | 12.5 | 12.5 | 6.25 | 6.25 | 25 | 12.5 | 12.5 | 400 |
| 10 | 25 | 25 | 12.5 | 50 | 25 | 25 | 12.5 | >800 |
| 11 | 25 | 50 | 25 | 50 | 75 | 75 | 25 | >800 |
| 18 | 25 | 25 | 6.25 | 6.25 | 25 | 6.25 | 12.5 | 400 |
| 21 | 25 | 50 | 6.25 | 6.25 | 50 | 50 | 25 | 400 |
| 22 | 50 | 25 | 12.5 | 25 | 50 | 25 | 50 | 400 | sents a halogen atom, a nitro group, a lower alkyl group or a lower alkoxy group, $n$ is an integer of 1 to 3 and when $n$ is 2 or 3, Y's may be the same or different.

2. The compound according to claim 1 wherein $R_1$ is a hydrogen atom or an alkyl group having 1 to 6 carbon atoms, $R_2$ is an alkyl group having 1 to 6 carbon atoms or an alkenyl group having 3 to 6 carbon atoms, X is a halogen atom, Y is a halogen atom, a nitro group, an alkyl group having 1 to 4 carbon atoms or an alkoxy group having 1 to 4 carbon atoms, $n$ is an integer of 1 to 3 and when $n$ is 2 or 3, Y's may be the same or different.

3. The compound according to claim 1 wherein $R_1$ is an alkyl group having 1 to 3 carbon atoms, $R_2$ is an alkyl group having 1 to 3 carbon atoms or an alkenyl group having 3 or 4 carbon atoms, X is a halogen atom, Y is a halogen atom, a nitro group, a methyl group or a methoxy group, $n$ is an integer of 1 or 2 and when $n$ is 2, Y's may be the same or different.

4. The compound according to claim 1 wherein $R_1$ is a methyl group, $R_2$ is a methyl group or a 2-propenyl group, X is a chlorine atom or a bromine atom, Y is a chlorine atom, a methyl group, a nitro group or a methoxy group, $n$ is an integer of 1 or 2 and when $n$ is 2, Y's may be the same or different.

5. The compound according to claim 1 wherein $R_1$ is a methyl group, $R_2$ is a methyl group or a 2-propenyl group, X is a chlorine atom or a bromine atom, $n$ is 2 and Y's are attached to the phenyl group at 2 and 4 positions and each Y represents a chlorine atom or Y at the 2-position is a chlorine atom and Y at the 4-position is a nitro group.

6. 1,3-Dimethyl-4-chloro-4-(2,4-dichlorobenzoyl)-5-pyrazolone.

7. 1,3-Dimethyl-4-bromo-4-(2,4-dichlorobenzoyl)-5-pyrazolone.

8. 1,3-Dimethyl-4-chloro-4-(2-chloro-4-nitrobenzoyl)-5-pyrazolone.

9. 1,3-Dimethyl-4-chloro-4-(2-nitro-5-methylbenzoyl)-5-pyrazolone.

10. 1-Ethyl-3-methyl-4-chloro-4-(2,4-dichlorobenzoyl)-5-pyrazolone.

11. 1-(2-Propenyl)-3-methyl-4-chloro-4-(2,4-dichlorobenzyl)-5-pyrazolone.

12. A herbicidal composition which comprises as an active ingredient a compound having the formula

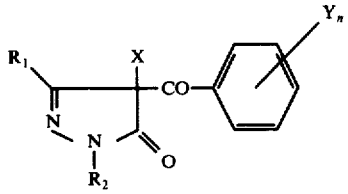

wherein $R_1$ represents a hydrogen atom or a lower alkyl group, $R_2$ represents a lower alkyl group or a lower alkenyl group, X represents a halogen atom, Y represents a halogen atom, a nitro group, a lower alkyl group or a lower alkoxy group, $n$ is an integer of 1 to 3 and when $n$ is 2 or 3, Y's may be the same or different and an agriculturally acceptable carrier.

13. The composition according to claim 12 wherein $R_1$ is a hydrogen atom or an alkyl group having 1 to 6 carbon atoms, $R_2$ is an alkyl group having 1 to 6 carbon atoms or an alkenyl group having 3 to 6 carbon atoms, X is a halogen atom, Y is a halogen atom, a nitro group, an alkyl group having 1 to 4 carbon atoms or an alkoxy group having 1 to 4 carbon atoms, $n$ is an integer of 1 to 3 and when $n$ is 2 or 3, Y's may be the same or different.

14. The composition according to claim 12 wherein $R_1$ is an alkyl group having 1 to 3 carbon atoms, $R_2$ is an alkyl group having 1 to 3 carbon atoms or an alkenyl group having 3 to 4 carbon atoms, X is a halogen atom, Y is a halogen atom, a nitro group, a methyl group or a methoxy group, $n$ is an integer of 1 or 2 and when $n$ is 2, Y's may be the same or different.

15. The composition according to claim 12 wherein $R_1$ is a methyl group, $R_2$ is a methyl group or a 2-propenyl group, X is a chlorine atom or a bromide atom, Y is a chlorine atom, a methyl group, a nitro group or a methoxy group, $n$ is an integer of 1 or 2 and when $n$ is 2, Y's may be the same or different.

16. The composition according to claim 12 wherein $R_1$ is a methyl group, $R_2$ is a methyl group or a 2-propenyl group, X is a chlorine atom or a bromine atom, $n$ is 2 and Y's are attached to the phenyl group at 2 and 4 positions and each Y represents a chlorine atom or Y at the 2-position is a chlorine atom and Y at the 4-position is a nitro group.

17. The composition according to claim 12 wherein said compound is selected from the group consisting of
1,3-dimethyl-4-chloro-4-(2,4-dichlorobenzoyl)-5-pyrazolone,
1,3-dimethyl-4-bromo-4-(2,4-dichlorobenzoyl)-5-pyrazolone,
1,3-dimethyl-4-chloro-4-(2-chloro-4-nitrobenzoyl)-5-pyrazolone,
1,3-dimethyl-4-chloro-4-(2-nitro-5-methylbenzoyl)-5-pyrazolone,
1-ethyl-3-methyl-4-chloro-4-(2,4-dichlorobenzoyl)-5-pyrazolone and
1-(2-propenyl)-3-methyl-4-chloro-4-(2,4-dichlorobenzoyl)-5-pyrazolone.

18. The composition according to claim 12 wherein said compound is contained in an amount of 0.1 - 99% by weight, based upon the composition.

19. A method for the destruction of undesirable weeds which comprises applying to said weeds a herbicidal amount of a compound having the formula

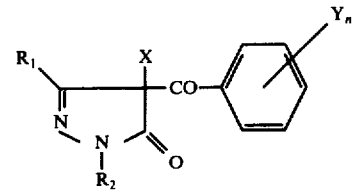

wherein $R_1$ represents a hydrogen atom or a lower alkyl group, $R_2$ represents a lower alkyl group or a lower alkenyl group, X represents a halogen atom, Y represents a halogen atom, a nitro group, a lower alkyl group or a lower alkoxy group, $n$ is an integer of 1 to 3 and when $n$ is 2 or 3, Y's may be the same or different.

20. The method according to claim 19 wherein $R_1$ is a hydrogen atom or an alkyl group having 1 to 6 carbon atoms, $R_2$ is an aklyl group having 1 to 6 carbon atoms or an alkenyl group having 3 to 6 carbon atoms, X is a halogen atom, Y is a halogen atom, a nitro group, an alkyl group having 1 to 4 carbon atoms or an alkoxy group having 1 to 4 carbon atoms, $n$ is an integer of 1 to 3 and when n is 2 or 3, Y's may be the same or different.

21. The method according to claim 19 wherein $R_1$ is an alkyl group having 1 to 3 carbon atoms, $R_2$ is an alkyl group having 1 to 3 carbon atoms or an alkenyl group having 3 to 4 carbon atoms, X is a halogen atom, Y is a halogen atom, a nitro group, a methyl group or a methoxy group, $n$ is an integer of 1 or 2 and when $n$ is 2, Y's may be the same or different.

22. The method according to claim 19 wherein $R_1$ is a methyl group, $R_2$ is a methyl group or a 2-propenyl group, X is a chlorine atom or a bromine atom, Y is a chlorine atom, a methyl group, a nitro group or a methoxy group, $n$ is an integer of 1 or 2 and when $n$ is 2, Y's may be the same or different.

23. The method according to claim 19 wherein $R_1$ is a methyl group, $R_2$ is a methyl group or a 2-propenyl group, X is a chlorine atom or a bromine atom, $n$ is 2 and Y's are attached to the phenyl group at 2 and 4 positions and each Y represents a chlorine atom or Y at the 2-position is a chlorine atom and Y at the 4-position is a nitro group.

24. The method according to claim 19 wherein said compound is selected from the group consisting of
1,3-dimethyl-4-chloro-4-(2,4-dichlorobenzoyl)-5-pyrazolone,
1,3-dimethyl-4-bromo-4-(2,4-dichlorobenzoyl)-5-pyrazolone,
1,3-dimethyl-4-chloro-4-(2-chloro-4-nitrobenzoyl)-5-pyrazolone,
1,3-dimethyl-4-chloro-4-(2-nitro-5-methylbenzoyl)-5-pyrazolone,
1-ethyl-3-methyl-4-chloro-4-(2,4-dichlorobenzoyl)-5-pyrazolone and
1-(2-propenyl)-3-methyl-4-chloro-4-(2,4-dichlorobenzoyl)-5-pyrazolone.

25. The method according to claim 19 wherein said herbicidal amount is within the range of 10 g to 4000 g of said compound per 10 ares.

* * * * *